United States Patent
Lunkenheimer et al.

[11] 3,935,312
[45] Jan. 27, 1976

[54] COMBATING FUNGI WITH IMIDAZO-[4,5-b]QUINOXALINES
[75] Inventors: Winfried Lunkenheimer; Karl Heinz Büchel, both of Wuppertal; Helmut Kaspers, Leverkusen, all of Germany
[73] Assignee: Bayer Aktiengesellschaft, Leverkusen, Germany
[22] Filed: Sept. 21, 1973
[21] Appl. No.: 399,652

[30] Foreign Application Priority Data
Oct. 7, 1972   Germany............................ 2249350

[52] U.S. Cl. ........ 424/250; 260/250 Q; 424/DIG. 8
[51] Int. Cl.² .......................................... A01N 9/22
[58] Field of Search .... 260/250 Q; 424/250, DIG. 8

[56] References Cited
UNITED STATES PATENTS

| | | | |
|---|---|---|---|
| 3,632,808 | 1/1972 | Brooker et al. | 260/240.4 |
| 3,663,543 | 5/1972 | Gulbenk et al. | 260/250 R |
| 3,723,419 | 3/1973 | Mee et al. | 260/240.6 |

OTHER PUBLICATIONS
Schipper, et al., J. Am. Chem. Soc., 73 (1951), pp. 5672–5675.
Röchling et al., Chem. Berichte 104 (1971), pp. 344–347.

Primary Examiner—Albert T. Meyers
Assistant Examiner—Allen J. Robinson
Attorney, Agent, or Firm—Burgess, Dinklage & Sprung

[57] ABSTRACT

Fungicidal compositions, containing and methods of combating fungi using, imidazo[4,5-b]quinoxalines of the general formula

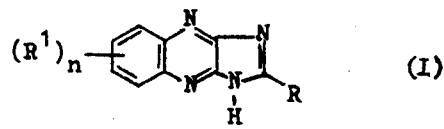

in which
R is lower alkyl or halo-lower alkyl,
$R^1$ is halogen, lower alkyl or halo-lower alkyl,
n is 0, 1 or 2.

7 Claims, No Drawings

COMBATING FUNGI WITH IMIDAZO-[4,5-b]QUINOXALINES

The present invention relates to and has for its objects the provision of particular new fungicidal compositions containing imidazo [4,5-b]quinoxalines, i.e., 2-alkyl- or -haloalkyl-imidazo[4,5-b]quinoxalines optionally substituted on the benzene ring by alkyl, halo or haloalkyl, in the form of mixtures with solid and liquid dispersible carrier vehicles, and methods for using such compounds in a new way especially for combating fungi and unwanted vegetation, with other and further objects becoming apparent from a study of the within specification and accompanying examples.

It has been disclosed in Angewandte Chemie 72 (1960), pages 973 et seq., that 6-methyl-quinoxaline-2,3-cycl.-dithiolcarbonate (Compound A) is fungicidally active. In particular, its action against powdery mildew fungi such as *Podosphaera leucotricha* or *Uncinula necator*, and against varieties of Erysiphe, should be singled out. However it is a disadvantage that an effect in most cases only manifests itself if the substance is applied above ground, for example on spraying or on fumigating the leaves and stems infected with mildew. Furthermore, the action is not always entirely satisfactory if relatively small quantities and low concentrations are used.

It has been found that imidazo[4,5-b]quinoxalines of the general formula

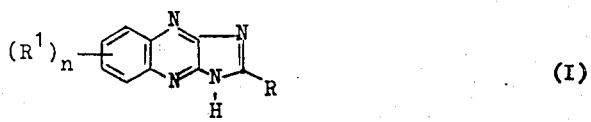

in which
R is lower alkyl or halo-lower alkyl,
$R^1$ is halogen, lower alkyl or halo-lower alkyl, and
n is 0, 1 or 2,
possesss excellent fungicidal properties.

Surprisingly, the imidazo-quinoxalines to be used according to the invention show a higher fungicidal action than 6-methyl-quinoxaline-2,3-cycl.-dithiolcarbonate, known in the art, which is chemically the nearest active compound of the same type of action. In addition, they show systemic fungicidal properties, in contrast to that known compound.

The formula (I) provides a general definition of the substances to be used according to the invention. R may represent straight-chain or branched alkyl with 1 to 4 carbon atoms (methyl, ethyl, n-propyl, i-propyl, n-butyl, i-butyl, sec.-butyl and tert.-butyl). Alternatively, R may represent haloalkyl, preferably with 1 or 2 carbon atoms and 2 to 5 halogen atoms, especially fluorine, for example trifluoromethyl or pentafluoroethyl. $R^1$ may represent halogen, especially chlorine, or straight-chain or branched alkyl with 1 to 4 carbon atoms, especially methyl, n-propyl, i-propyl and tert.-butyl, or it may represent haloalkyl, preferably with 1 or 2 carbon atoms and 2 to 5 halogen atoms, especially fluorine or chlorine. The trifluoromethyl, the pentafluoroethyl, the chloromethyl and the chloroethyl radical may be mentioned as examples.

The following may be mentioned as examples of the substances to be used according to the invention: 6-chloro-2-ethyl-1H-imidazo[4,5-b]quinoxaline, 6-chloro-2-methyl-1H-imidazo[4,5-b]quinoxaline, 2-ethyl-1H-imidazo[4,5-b]quinoxaline, 2-ethyl-6-methyl-1H-imidazo[4,5-b]quinoxaline, 2-propyl-1H-imidazo[4,5-b]quinoxaline, 6-chloro-2-propyl[4,5-b]-quinoxaline, 2-isobutyl-1H-imidazo[4,5-b]quinoxaline, 6-chloro-2-isobutyl-1H-imidazo[4,5-b]quinoxaline, 2-isopropyl-1H-imidazo[4,5-b]quinoxaline, 5,7-dichloro-2-trifluoromethyl-1H-imidazo[4,5-b]quinoxaline and 6,7-dichloro-2-trifluoromethyl-1H-imidazo[4,5-b]quinoxaline.

Some of the compounds to be used according to the invention are known (J. Am. Chem. Soc. 73 (1951), 5,676 and Chem. Berichte 104 (1971), 346). The compounds which are not yet known can be prepared according to processes described there, for example by reaction of 2,3-diamino-quinoxalines (which can be prepared from diaminobenzenes and cyanogen or 2,3-dichloro-quinoxalines) with acid chlorides or acid anhydrides at temperatures from 80° to 200°C, optionally using high-boiling solvents such as xylene, piperdine or pyridine or anhydrous fatty acids as diluents (see Example 1) Alternatively, the compounds of the formula (I) which are not yet known can be prepared by heating 2,3-dichloroquinoxalines with liquid ammonia and aliphatic nitriles at temperatures of 130°–200°C, preferably at about 150°C, and pressures of 10 to 20 atmospheres gauge, preferably 15 atmospheres gauge, in an autoclave (see Example 5). To isolate the active compounds according to the invention, the solvent may be distilled off in vacuo, the residue taken up in dilute alkali metal hydroxide solution, the mixture filtered, the filtrate acidified and the precipitate filtered off and optionally purified by recrystallization.

A preferred compound for use according to the invention is 6-chloro-2-ethyl-1H-imidazo[4,5-b]quinoxaline. This compound, which is new, is distinguished by a considerable activity.

The active compounds to be used according to the invention show a strong fungitoxic action. They do not normally harm crop plants in the concentrations required for combating fungi and have a low toxicity towards warm-blooded animals. For these reasons, they are suitable for use as plant protection agents for combating fungi, and may be applied for this purpose to an area in which crops are grown.

Fungitoxic agents are employed in plant protection for combating Archimycetes, Phycomycetes, Ascomycetes, Basidiomycetes and *Fungi Imperfecti*.

The active compounds for use according to the invention have a very broad spectrum of action and can be used against parasitary fungi which attack above-ground parts of plants or which attack plants through the soil.

They display a particularly good activity against parasitary fungi of the class of the Ascomycetes, such as *Erysiphe* species, *Podosphaera* species and *Venturia* species, for example against the pathogen of powdery mildew of apples (*Podosphaera leucotricha*) and of powdery mildew of cucumber (*Erysiphe cichoracearum*).

The systemic activity of the active compounds for use according to the invention is worthy of particular mention. Thus it proves possible to protect plants against fungal attack if the active compound is supplied to the above-ground parts of the plant through the soil and the root or through dressing the seed or plant.

The active compounds according to the invention have a low toxicity towards warm-blooded animals and can easily be handled, because of their low odor and their good toleration by human skin.

The active compounds according to the instant invention can be utilized, if desired, in the form of the usual formulations or compositions with conventional inert (i.e., plant compatible or herbicidally inert) pesticide diluents or extenders, i.e., diluents, carriers or extenders of the type usable in conventional pesticide formulations or compositions, e.g., conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes (e.g., cyclohexane, etc.), paraffins (e.g., petroleum or mineral oil fractions), chlorinated aliphatic hydrocarbons (e.g., methylene chloride, chloroethylenes, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; as well as inert dispersible finely divided solid carriers, such as ground natural minerals (e.g., kaolins, clays, alumina, silica, chalk, i.e., calcium carbonate, talc, attapulgite, montmorillonite, kieselgur, etc.) and ground synthetic minerals (e.g., highly dispersed silicic acid, silicates, e.g., alkali silicates, etc.); whereas the following may be chiefly considered for use as conventional carrier vehicle assistants, e.g., surface-active agents, for this purpose: emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides and herbicides, or insecticides, acaricides, rodenticides, bactericides, nematocides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g., a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g., average particle diameter of from 50–100 microns, or even less, i.e., mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used as leaf fungicides, the active compounds are generally about 0.05 to 0.0001% by weight, preferably about 0.01 to 0.001%, of the compositions.

When used in the watering and dressing methods, amounts of active compound of between 1,000 and 1 ppm, preferably of 100 to 10 ppm, are generally required per ml of liquid.

The active compounds have some herbicidal effects, especially if amounts of 0.05 to 0.1 percent by weight are used in post-emergence application.

Furthermore, the present invention contemplates methods of selectively killing, combating or controlling fungi, which comprises applying to at least one of correspondingly (a) such fungi and (b) the corresponding habitat thereof, i.e., the locus to be protected, a correspondingly combative or toxic amount, i.e., a fungicidally or herbicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Erysiphe test
Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoreacearum*. The plants were subsequently placed in a greenhouse at 23°–24°C and at a relative atmospheric humidity of about 75%.

After 12 days, the infection of the cucumber plants was determined as a percentage of the untreated but also inoculated control plants. 0% means no infection; 100% means that the infection was exactly as great as in the case of the control plants.

The active compounds, the concentrations of the active compounds and the results can be seen from Table 1.

Table 1

Erysiphe test

| Active compound | Infection in % of the infection of the untreated control at an active compound concentration of 0.00156% |
|---|---|
| (known) (A) | 35 |
| (2) | 22 |
| (10) | 0 |
| (1) | 0 |
| (7) | 27 |
| (9) | 22 |

EXAMPLE 2

Erysiphe test/systemic
Solvent: 4.7 parts by weight of acetone
Dispersing agent: 0.3 part by weight of alkylaryl polyglycol ether
Water: 95 parts by weight The amount of the active compound required for the desired concentration of active compound in the watering liquid was mixed with the stated amount of the solvent, and the concentrate was diluted with the stated amount of water containing the stated additions.

Cucumber plants grown in standard soil, in the 1–2 leaf stage, were watered three times within 1 week with 20 ml of the watering liquid, having the stated concentration of active compound, per 100 cc of soil.

After the treatment, the plants treated in this way were inoculated with conidia of the fungus *Erysiphe cichoracearum*. The plants were subsequently placed in a greenhouse at 23°–24°C and at a relative atmospheric humidity of 70%. After 12 days, the infection of the cucumber plants was determined as a percentage of the untreated but also inoculated control plants.

0% means no infection, and 100% means that the infection was exactly as great as in the case of the control plants.

The active compounds, the concentrations of the active compounds and the results can be seen from Table 2.

Table 2

Erysiphe test / systemic

| Active compound | Infection in % of the infection of the untreated control at an active compound concentration of | | |
|---|---|---|---|
| | 120 ppm | 30 ppm | 10 ppm |
| (known) (A) | 100 | | |
| (2) | 0 | | |
| (10) | 0 | | |

Table 2—Continued

Erysiphe test/systemic

| Active compound | Infection in % of the infection of the untreated control at an active compound concentration of | | |
|---|---|---|---|
| | 120 ppm | 30 ppm | 10 ppm |
| 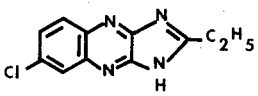 (1) | | | 0 |
| 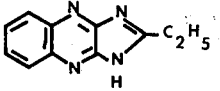 (6) | | | 21 |
| 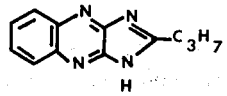 (9) | | | 25 |

EXAMPLE 3

Podosphaera test/systemic
Solvent: 4.7 parts by weight of acetone
Dispersing agent: 0.3 part by weight of alkylaryl polyglycol ether
Water: 95 parts by weight The amount of active compound required for the desired concentration of the active compound in the watering liquid was mixed with the stated amount of solvent and the concentrate was diluted with the stated amount of water which contained the stated additions.

Apple seedlings grown in standard soil, in the 3–4 leaf stage, were watered once within a week with 20 ml of the watering liquid, having the stated concentration of active compound, per 100 cc of soil.

After the treatment, the plants treated in this way were inoculated with conidia of *Podosphaera leucotricha* Salm and placed in a greenhouse at a temperature of 21°–23°C and a relative atmospheric humidity of approximately 70%. 10 Days after the inoculation, the infection of the seedlings was determined as a percentage of the untreated but also inoculated control plants.

0% means no infection and 100% means that the infection was exactly as great as in the case of the control plants.

The active compounds, the concentrations of the active compounds and the results can be seen from Table 3.

Table 3

Podosphaera test/systemic

| Active compound | Infection in % of the infection of the untreated control at an active compound concentration (in %) of | |
|---|---|---|
| | 100 ppm | 30 ppm |
| 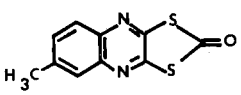 (A) (known) | 80 | |
| 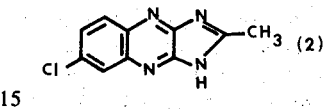 (2) | 47 | |
| 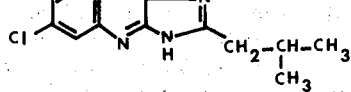 (19) | 41 | |
| 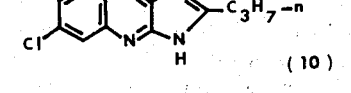 (10) | 24 | 27 |
| 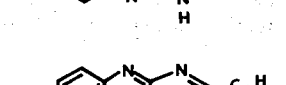 (1) | 11 | 44 |
| 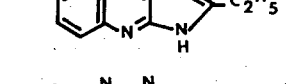 (6) | 41 | |
| 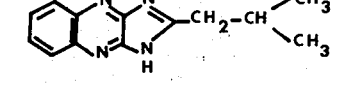 (18) | 11 | |

The following examples illustrate the synthesis of the compounds.

EXAMPLE 4:

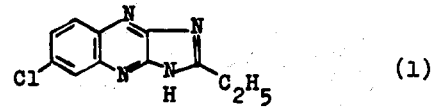 (1)

a. 6-Chloro-2,3-diamino-quinoxaline required as starting material was prepared as follows: 233.5 g (1 mole) of 2,3,6-trichloro-quinoxaline and 10 g (0.1 mol) of copper-I chloride were suspended in 2 liters of anhydrous methanol and 450 ml (approximately 20 moles) of liquid ammonia were added thereto. The reaction mixture was heated for 12 hours to 150°C in a steel autoclave of 5 liters capacity. In the course thereof, a pressure of 15 atmospheres gauge was set up. After cooling, the reaction mixture was filtered, the filtreate was freed of the solvent in vacuo and the residue was recrystallized from pyridine. 95 g (representing 49% of theory) of 6-chloro-2,3-diamino-quinoxaline were obtained.

b. In an alternative procedure, the starting material was prepared as follows:

60 G (1.15 moles of cyanogen, which had beforehand been freed of adhering hydrocyanic acid by washing with a silver nitrate solution containing nitric acid and had been condensed in a cold trap, were passed at room temperature into a solution of 71.3 g (0.5 mole) of 1-chloro-3,4-diaminobenzene and 2 ml of 10% strength sodium hydroxide solution in 200 ml of anhydrous methanol. The reaction mixture was left to stand for 2 days at room temperature. Thereafter the resulting precipitate was filtered off, rinsed with a little methanol and dried. 41.6 G (representing 43% of theory) of 6-chloro-2,3-diamino-quinoxaline of melting point 290°C were obtained.

c. 78 G (0.4 mole) of 6-chloro-2,3-diamino-quinoxaline were dissolved in 500 ml of anhydrous propionic acid and 105 g (0.8 mole) of propionic anhydride were added thereto. The reaction mixture was heated to the boil under reflux for 5 hours. After cooling, the solvent was distilled off in vacuo, the residue was taken up in dilute sodium hydroxide solution, the mixture was filtered, the filtrate was acidified with dilute hydrochloric acid and the resulting precipitate was filtered off. It was well washed with water and dried in vacuo at 110°C. 82 g (representing 88% of theory) of 6-chloro-2-ethyl-1H-imidazo[4,5-b]quinoxaline of melting point 190°C (decomposition) were obtained.

EXAMPLE 5:

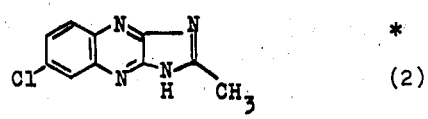

23.4 G (0.1 mole) of 2,3,6-trichloroquinoxaline and 1 g of copper-I chloride (approximately 0.1 mole) were dissolved in 250 ml of anhydrous acetonitrile and 45 ml (approximately 2 moles) of liquid ammonia were added thereto. The reaction mixture was heated for 12 hours to 150°C in a steel autoclave of 0.7 liter capacity. In the course thereof, a pressure of 10 to 15 atmospheres gauge was set up. The crystalline precipitate produced after cooling was filtered off and dissolved in dilute sodium hydroxide solution. The solution was filtered, the filtrate was acidified with hydrochloric acid and the precipitate was filtered off, well rinsed with water and recrystallized from 30% strength acetic acid. 10 g (representing 46% of theory) of 6-chloro-2-methyl-1H-imidazo[4,5-b]quinoxaline of melting point >300°C were obtained.

The compounds identified in Table 4 were prepared in an analogous manner. The compounds marked with an asterisk are known from the literature.

Table 4

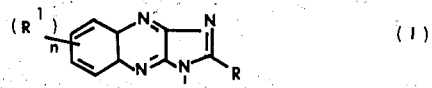

| Cpd. No. | $R^1$ | n | R | Melting point (°C) | |
|---|---|---|---|---|---|
| 3 | 6—$CH_3$ | 1 | $CH_3$ | 310 | (decomposition) |
| 4 | — | 0 | $CH_3$ | >280 | (decomposition) |
| 5 | 6—$C(CH_3)_3$ | 1 | $CH_3$ | 320 | (decomposition) |
| 6 | — | 0 | $C_2H_5$ | >300 | (decomposition) |
| 7 | 6—$CH_3$ | 1 | $C_2H_5$ | 230 | (decomposition) |
| 8 | 6—$C(CH_3)_3$ | 1 | $C_2H_5$ | 230 | |
| 9 | — | 0 | $C_3H_7$ | 250 | (decomposition) |
| 10 | 6—Cl | 1 | $C_3H_7$ | 270 | |
| 11* | 6—$CH_3$ | 1 | $C_3H_7$ | 271 | |
| 12 | 6—$C(CH_3)_3$ | 1 | $C_3H_7$ | 220 | |
| 13 | — | 0 | $CH(CH_3)_2$ | 235 | |
| 14 | 6—Cl | 1 | $CH(CH_3)_2$ | 280–300 | (decomposition) |
| 15* | 6—$CH_3$ | 1 | $CH(CH_3)_2$ | 250 | |
| 16* | — | 0 | $C_4H_9$ | 250 | |
| 17 | 6—Cl | 1 | $C_4H_9$ | 240 | (decomposition) |
| 18 | — | 0 | $CH_2$—CH—$CH_3$<br>　　　　$CH_3$ | 233 | (decomposition) |
| 19 | 6—Cl | 1 | $CH_2$—CH—$CH_3$<br>　　　　$CH_3$ | 245 | |
| 20 | 6—$C(CH_3)_3$ | 1 | $CH_2$—CH—$CH_3$<br>　　　　$CH_3$ | 265 | |
| 21 | — | 0 | $CF_3$ | 270 | |
| 22 | 6—Cl | 1 | $CF_3$ | 225 | |
| 23 | 6—$CH_3$ | 1 | $CF_3$ | 212 | |
| 24 | 6—$C_4H_9$ | 1 | $CF_3$ | 260 | |
| 25* | 5,7—$Cl_2$ | 2 | $CF_3$ | 360 | |
| 26* | 6,7—$Cl_2$ | 2 | $CF_3$ | 272 | |

It will be appreciated that the instant specification and examples are set forth by way of illustration and not limitation, and that various modifications and changes may be made without departing from the spirit and scope of the present invention.

What is claimed is:

1. A method of combating parasitary fungi which attack plants which comprises applying to said fungi a fungicidally effective amount of an imidazo[4,5-b]quinoxaline of the formula

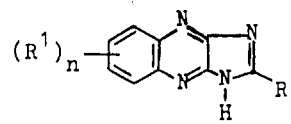

in which

R is alkyl with 1 to 4 carbon atoms or haloalkyl with 1 to 2 carbon atoms and 2 to 5 halogen atoms, R[1] is chlorine, alkyl with 1 to 4 carbon atoms or haloalkyl with 1 to 2 carbon atoms and 2 to 5 halogen atoms, and n is 0, 1 or 2.

2. The method according to claim 1 in which R is alkyl of 1 to 4 carbon atoms or haloalkyl of 1 or 2 carbon atoms and 2 to 5 fluorine atoms, and R[1] is chlorine, methyl, n-propyl, iso-propyl, tert.-butyl, or haloalkyl of 1 or 2 carbon atoms and 2 to 5 fluorine or chlorine atoms.

3. A method of combating parasitary fungi which attack plants which comprises applying to said fungi or a habitat thereof a fungicidally effective amount of 6-chloro-2-ethyl-1H-imidazo[4,5-b]quinoxaline of the formula

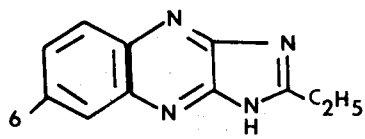

4. A method of combating parasitary fungi which attack plants which comprises applying to said fungi or a habitat thereof a fungicidally effective amount of 6-chloro-2-methyl-1H-imidazo[4,5-b]quinoxaline of the formula

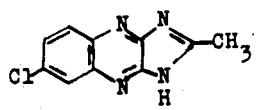

5. A method of combating parasitary fungi which attack plants which comprises applying to said fungi or a habitat thereof a fungicidally effective amount of 2ethyl-1H-imidazo[4,5-b]quinoxaline of the formula

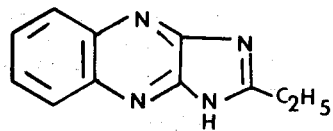

6. A method of combating parasitary fungi which attach plants which comprises applying to said fungi or a habitat thereof a fungicidally effective amount of 2-propyl-1H-imidazo[4,5-b]quinoxaline of the formula

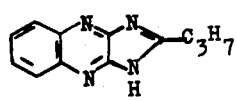

7. A method of combating parasitary fungi which attach plants which comprises applying to said fungi or a habitat thereof a fungicidally effective amount of 6-chloro-2-propyl-1H-imidazo[4,5-b]quinoxaline of the formula

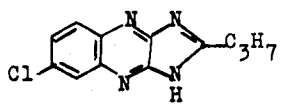

* * * * *

UNITED STATES PATENT OFFICE
CERTIFICATE OF CORRECTION

PATENT NO. : 3,935,312
DATED : January 27, 1976
INVENTOR(S) : Winfried Lunkenheimer et al It is certified that error appears in the above-identified patent and that said Letters Patent are hereby corrected as shown below:

Column 12, Claim 6, line 15, correct spelling of "attack".

Column 12, Claim 7, line 27, correct spelling of "attack".

Column 11, Claim 3, structural formula, cancel "6" and substitute -- Cl --.

Signed and Sealed this

Thirty-first Day of August 1976

[SEAL]

Attest:

RUTH C. MASON
Attesting Officer

C. MARSHALL DANN
Commissioner of Patents and Trademarks